US006943016B1

(12) United States Patent
Ridet et al.

(10) Patent No.: US 6,943,016 B1
(45) Date of Patent: Sep. 13, 2005

(54) HUMAN ADULT ASTROCYTES, THEIR PREPARATION AND USES THEREOF

(75) Inventors: Jean-Luc Ridet, Lausanne (CH); Jacques Mallet, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/868,026

(22) PCT Filed: Jan. 5, 2000

(86) PCT No.: PCT/IB00/00165

§ 371 (c)(1),
(2), (4) Date: Jan. 11, 2002

(87) PCT Pub. No.: WO00/40699

PCT Pub. Date: Jul. 13, 2000

Related U.S. Application Data

(60) Provisional application No. 60/114,758, filed on Jan. 5, 1999.

(51) Int. Cl.[7] ............................ C12N 5/02; C12N 5/06; C12N 5/08

(52) U.S. Cl. ..................... 435/325; 435/352; 435/353; 435/354; 435/363; 435/366; 435/368

(58) Field of Search ................................. 435/325, 352, 435/353, 354, 363, 366, 368, 440, 455, 458, 456

(56) References Cited

U.S. PATENT DOCUMENTS

| 5,202,120 A | * | 4/1993 | Silver et al. .................... 424/93 |
| 5,627,047 A | * | 5/1997 | Brenner et al. ............. 435/69.1 |
| 5,650,148 A | * | 7/1997 | Gage et al. ................. 424/93.2 |
| 5,750,376 A | * | 5/1998 | Weiss et al. .............. 435/69.52 |

FOREIGN PATENT DOCUMENTS

| WO | WO 91/06631 | 5/1991 |
| WO | WO 94/01135 | 1/1994 |

OTHER PUBLICATIONS

Wu and Schwartz (Mar. 15, 1998) "Cell Culture Models for Reactive Gliosis: New Perspectives." Journal of Neuroscience Research 51(6): 675–681.*
Adrien, J. et al., Biochemical and Electrophysiological evidence for an agonist action of CM57493 at pre– and post–synaptic 5–HT1A receptors in Brain, J. Pharmacol. Exp. Ther. 248:1222–1230 (1989).
Aloisi, F. et al., Astrocyte Cultures from Human Embryonic Brain: Characterization and modulation of Surface Molecules by Inflammatory Cytokines, J. Neurosci. Res. 32:494–506 (1992).
Aubert, I. et al., Regeneration in the Adult Mammalian CNS: Guided by Development., Curr. Opin. Neurobiol. 5:625–635 (1995).
Bilang–Bleuel et al., Intrastriatal Injection of an Adenoviral Vector Expressing GDNF Prevents Dopaminergic Neuron Degeneration and Behavioral Impairment in a Rat Model of Parkinson's Disease, Proc. Natl. Acad. Sci. USA 94:8818–8823 (1997).
Castillo Jr. et al., Reginal Ganglion Cell survival is Promoted by Genetically Modified Astrocytes designed to Secrete Brain–Derived Neutrophic Factor (BDNF), Brain Res. 647:30–37 (1994).
Corti et al., Intracerebral Tetracycline–dependent Regulation of Gene Expression in Grafts of Neural Precursors., NeuroReport 7:1655–1659 (1996).
Cunningham et al., The Use of Genetically Altered Astrocytes to Provide Nerve Growth Factor (NGF) to Adrenal Chromaffin Cell Grafted into the Striatum. , Brain Res. 561:192–202 (1991).
Cunningham et al., Nerve Growth Factor Released by Transgenic Astrocytes enhanced the Function Adrenal Chromaffin Cell Grafts in a Rat Model of Parkinson's Disease, Brain Res. 568:219–223 (1994).
Fisher et al., Grafting in the Mammalian Central Nervous System, Physiol. Rev. 73:583–616 (1993).
Fisher, L.J., Neural Precursor Cells: Applications for the Study and Repair of the Central Nervous System. , Neurobiol. Dis. 4:1–22 (1997).
Fisher et al., Survial and Function of Intrastriatally grafted Fibroblasts Genetically modified to Produce L–DOPA., Neuron 6:371–380 (1996).
Fritschy et al., Brain Cell Type Specificity and Gliosis–Induced Activation of the Human Cytomegalovirus Immediate–Early Promoter in Transgenic Mice., J. Neurosci. 16:2275–82 (1996).
Gage et al., Isolation, Characterization and Use of Stem Cells from the CNS., Ann. Rev. Neurosci. 18:159–192 (1995).
Goodman et al., Adenoviral–mediated Thymidine Kinase Gene Transfer into the Primate Brain followed by Systemic Ganciclovir: Pathologic, Radiologic and Molecular Studies., Human Gene Ther. 7:1241–1250 (1996).
Gossen et al., Tight Control of Gene Expression in Mammalian Cells by Tetacylcine–responsive Promoters, Proc. Natl. Acad. Sci. USA 89:5547–5551 (1992).
Gossen et al., Transcriptional Activation by Tetracyclines in Mammalian Cells, Science 268:1766–1769 (1995).
Horellou et al., In vivo Release of DOPA and Dopamine from Genetically Engineered Cells and Grafted to the Denervated Striatum., Neuron 5:393–402 (1990a).
Horellou et al., Behavioral Effect of Engineered Cells that synthesize L–DOPA or Dopamine after Grafting into the Rat Neostriatum, Eur. J. Neurosci. 2:116–119 (1990b).

(Continued)

*Primary Examiner*—Elizabeth C. Kimmerer
*Assistant Examiner*—Christopher James Nichols
(74) *Attorney, Agent, or Firm*—Nixon & Vanderhye P.C.

(57) ABSTRACT

The invention provides an essentially pure preparation of human adult astrocytes, and a method of producing same. The purified astrocytes are useful for the treatment of neurodegenerative disorders or trauma to the central nervous system.

10 Claims, 5 Drawing Sheets

OTHER PUBLICATIONS

Horellou et al., Direct Intracerebral Gene Transfer of an Adenoviral Vector Expressing Tyrosine Hydroxylase in a Rat Model of Parkinson's Disease, NeuroReport 6:49–53 (1994).

Juorio et al., Decarboxylation of L–DOPA by Cultured Astrocytes., Brain Res. 626:49–53 (1993).

Kistner et al., Doxycycline–mediated Quantitative and Tissue–specific Control of Gene Expression in Transgenic Mice., Proc. Natl. Acad. Sci. USA 93:10933–10938 (1996).

Kojima et al., Adenovirus–mediated Transduction with Human Glial Cell Line–derived Neurotrophic Factor Gene Prevents 1–methyl–4–phenyl–1,2,3,6–tetrahydropyridine–induced Dopamine Depletion in Striatum of Mouse Brain, Biochem. Biophys. Res. Commun. 238:569–573 (1997).

La Gamma et al., Genetically Modified Primary Astrocytes as Cellular Vehicles for Gene Therapy in the Brain., Cell Transplant. 2:207–214 (1993).

Levallois et al., An Adenovirus Vector Encoding Tyrosine Hydroxylase Activity may Enter Human CNS cells in Primary Dissociated Cultures., Int. J. Dev. Neurosci. 14:613–619 (1996).

Lin et al., Human Fetal Astrocytes in an Ex Vivo Gene Therapy Vehicle for Delivering Biologically Active Nerve Growth Factor, Hum. Gene Ther. 8:331–339 (1997).

Lundberg et al., Generation of DOPA–producing Astrocytes by Retroviral Transduction of the Human Tyrosinase Hydroxylase Gene: In vivo Characterization and In vivo Effects in the Rat Parkinson Model, Exp. Neurol. 139:39–53 (1996).

Maron et al., Differential Toxicity of Ganciclovir for Rat Neurons and Astrocytes in Primary Culture following Adenovirus–Mediated Transfer of the HSVtk Gene, Gene Ther. 4:25–31 (1997).

Martinez–Serrano et al., Immortalized Neural Progenitor Cells for CNS Gene Transfer and Repair, Trends Nerosci. 20: 530–538 (1997).

Miller et al., Progress in Transcriptionally Targeted and Regulatable Vectors for Gene Therapy, Hum. Gene Ther. 8:803–815 (1997).

Olanow et al., Fetal Nigral Transplantation as a Therapy for Parkinson's Disease, Trends Neruosci. 19:102–109 (1996).

Perzelova et al., Appearance of GFAP–Positive Cells in Adult Human Brain Cultures Spontaneously Decelerated in Growth, Glia 7:237–244 (1993).

Pundt et al., The Fate of Human Glial Cells Following Transplantation in Normal Rodents and Rodent Models of Neurodegenerative Disease, Brain Res. 695:25–36 (1995).

Reinhard et al., A Rapid and Sensitive Assay for Tyrosine–3–Monooxygenase Based Upon theRelease of 3H20 and Adsorption of [3H]–Tyorsine by Charcoal, Life Sci. 39:2185–2189 (1986).

Ridet et al., Reactive Astrocytes: Cellular and Molecular Cues to Biological Function., Trends Neruosci. 20:570–577 (1997).

Ridoux et al., The use of Adenovirus Vectors for Intracerebral Grafting of Transfecting Nervous Cells, NeuroReport 5:801–804 (1994).

Sabate et al., Transplantation to the Rat Brain of Human Neuroal Progenitors that were Genetically Modified using Adenovirus., Nature Genet. 9:256–260 (1995).

Saez et al., Inducible Gene Expression in Mammalian Cells and Transgenic Mice , Curr. Opin. Biotechnol. 8:608–616 (1997).

Shockett et al., A Modified tetracycline–Regulated System Provides Autoregulatory, Inducible Gene Expression in Cultured Cells and Transgenic Mice., Proc. Natl. acad. Sci. USA 92:6522–6526 (1995).

Stachowiak et al., Growth Factor Regulation of Cell Groth and Proliferation in the Nervous System, Mol. Neurobiol. 15:257–283 (1997).

Streit, W.J., An Improved Staining Method for Rat Microglial Cells Using the Lectin from Griffonia Simplicifolia (GSA I–B4), J. Histochem. Cytochem. 38:1683–1686 (1990).

Taylor, R., Cell Vehicles for Gene Transfer to the Brain, Neuromuscal. Dis. 7:343–351 (1997).

Wolff et al., Grafting Fibroblasts Genetically Modified to Produce L–DOPA in a Rat Model of Parkinson's Disease, Proc. Natl. Acad. Sci. USA 86:9011–9014 (1989).

Yong et al., Gamma–interferon Promoters Proliferation of Adult Human Astrocytes In Vitro and Reactive Gliosis in the Adult Mouse Brain In Vivo., Proc. Natl. acad. Sci. USA 88:7016–7020 (1991).

Yoshimoto et al., Astrocytes Retroviraly Transduced with BDNF Elicit Behavioral Improvement in a Rat Model of Parkinson's Disease, Brain Res. 691:25–36 (1995).

De Groot et al., Establishment of Human Adult Astrocyte Cultures Derived from Postmortem Multiple clerosis and Control Brain and Spinal Cord Regions, J. Neurosci. Res. 49(3):342–354 (1997).

Ridet et al., Toward Autologous Ex Vivo Gene Therapy for the Central Nervous system with Human Adult Astrocytes, Human Gene Therapy 10(2):271–280 (1999).

* cited by examiner

HUMAN ADULT ASTROCYTES, THEIR PREPARATION AND USES THEREOF

The present application is a 371 U.S. National Phase of PCT/IB00/00165, filed 5 Jan. 2000, which designated the U.S., and claims benefit of U.S. Provisional Application Ser. No. 60/114,758, filed 5 Jan. 1999.

FIELD OF THE INVENTION

This invention relates to the field of neurobiology. More specifically, it relates to purified human adult astrocytes, to methods for their preparation, and to their use, especially for the treatment of neurodegenerative disorders or trauma to the central nervous system.

BACKGROUND OF THE INVENTION

Astrocytes

The combination of cell transplantation and gene transfer techniques provides a therapeutic approach to neurodegenerative diseases and traumatic injury. Several cell types, e.g. progenitor cells, neurons, glial cells, fibroblasts and myoblasts, have been investigated as vehicles for gene delivery to the central nervous system (CNS) (Wolff et al., 1989; Horellou et al., 1990a,b; Fisher et al., 1991, 1993, Gage et al., 1995; Sabate et al., 1995; Fisher, 1997; Martinez-Serrano and Bjorklund, 1997). Particular attention has been paid to the therapeutic activity of genetically engineered astrocytes (Cunningham et al. 1991, 1994; La Gamma et al., 1993; Castillo et al., 1994: Pundt et al., 1995; Lundberg et al., 1996; Lin et al., 1997). Astrocytes are especially targeted for brain repair because they are normal CNS constituents, are endowed with efficient secretory mechanisms and provide support to neurons through the release of trophic factors that promote their survival, differentiation and regeneration In addition, they can be expanded in culture and genetically engineered to express foreign transgenes. Recently, human fetal astrocytes arising from legal abortions have been cultured and successfully transduced with a retrovirus driving the expression of active NGF (Lin et al., 1997).

Human adult astrocytes are more relevant for human brain repair, since they allow autologous ex vivo gene transfer, thus obviating immunological rejection and side effects of immunosuppressors. In recent studies that attempted to culture human adult astrocytes, contamination with microglial cells was reported (Yong et al., 1991, 1992).

Gene Therapy

Ex vivo gene transfer involves the delivery of therapeutic cells to a patient (Wolff et al., 1989; Horellou et al., 1990a,b; Fisher et al., 1991, 1993, Gage et al., 1995; Sabate et al., 1995; Fisher, 1997; Martinez-Serrano and Bjorklund, 1997; Taylor, 1997). The use of immortalized cell lines for gene therapy is of limited value, since they retain tumorigenic properties. In contrast, primary cultured cells are more suitable. One of the best cell types for ex vivo gene transfer and subsequent transplantation is astrocytes (La Gamma et al., 1993; Castillo et al., 1994; Cunningham et al., 1994; Ridoux et al., 1994; Pundt et al., 1995; Lundberg et al., 1996; Lin et al., 1997), which are normally present in the CNS as the major supporting cells with efficient secretory machinery. Grafted .astrocytes, previously modified to produce enzymes, neurotransmitters or trophic factors, a can integrate and function suitably in the CNS (see refs in Taylor, 1997). Rat primary cultured astrocytes have been genetically engineered to produce NGF and BDNF, and survive after transplantation into the brain (Cunningham et al., 1991, 1994; Yoshimoto et al., 1995).

Recently, the interest in human astrocytes has grown (Yong et al., 1991, 1992: Aloisi et al., 1992; Perzelova and Mares, 1993; Pundt et al., 1995; Lin et al. 1997). Yong and colleagues (1992) reported that up to 80% of primary cultured cells were macrophages/microglial cells. After removal of most of the oligodendrocytes and microglial cells, 70% of the cells were astrocytes (Yong et al., 1992). The presence of microglial cells in astrocyte cultures may cause undesirable effects both in vitro and in vivo, since they proliferate actively and are major components of the immune cell population. Therefore, there is a need for a method to produce a population of astrocytes that is free of contaminating microglial cells. The present invention addresses this need, as discussed below. The present invention overcomes the disadvantages of impure preparations of astrocytes, and provides a cell preparation suitable for treating trama to the CNS and for the treatment of neurodegenerative disorders, such as Parkinson's, Huntington's or Alzheimer's disease.

The citation of any reference herein should not be construed as an admission that such reference is available as "Prior Art" to the instant application.

SUMMARY OF THE INVENTION

The present invention provides purified astrocytes and methods for their preparation. In a preferred embodiment, the astrocytes are human, adult astrocytes.

Therefore, the invention provides a method of producing an essentially pure population of astrocytes comprising: a) introducing a preparation of astrocytes to a culture vessel, b) incubating the astrocytes from step a) under conditions enabling attachment of the astrocytes to the culture vessel, and c) removing cells which have not attached to the culture vessel at a time of about 48 hours from the beginning of step a). By being "essentially pure" the cell population is at least 75% astrocytes, preferably at least 85% astrocytes, more preferably at least about 95% astrocytes, and most preferably greater than about 98% astrocytes. The term "about" means within 20%, preferably within 10%, and more preferably within 5% of a given value or range. A "culture vessel" can be any support suitable for cell attachment and growth including, but not limited to, a culture dish or flask.

In a preferred embodiment, the astrocytes are human astrocytes. More preferably, they are human adult astrocytes.

Astrocytes produced according to the present invention are essentially free of microglial cells. That is, the presence of microglial cells is not detected by OX42 immunostaining and labeling with $B_4$ isolectin from *Giffionia simplicifolia*.

In one aspect of the method of the invention, an exogenous nucleic acid may be introduced into the astrocytes. The nucleic acid may be introduced into the astrocytes with a viral vector, by calcium-phosphate precipitation, liposome-mediated transfection, cationic lipid transfection, or lipopolyamine-mediated transfection. Preferably, the nucleic acid encodes a neuroactive substance.

The invention also provides an essentially pure population of astrocytes. Preferably, the astrocytes are human astrocytes. More preferably, they are human adult astrocytes. A population of astrocytes produced according to the present invention is essentially free of microglial cells.

In one aspect of the invention, the population of astrocytes comprises an exogenous nucleic acid in a preferred embodiment, the nucleic acid encodes a neuroactive substance. The nucleic acid may be DNA or RNA. In one aspect, the nucleic acid is a DNA encoding a protein, polypeptide or peptide. The protein, polypeptide or peptide may be a growth factor, neurotrophic factor, or enzyme. Alternatively, the nucleic acid may be a DNA encoding an antisense-RNA or a ribozyme. In a preferred embodiment, the nucleic acid is operably linked to a regulatory region comprising a regulatable promoter, an inducible promoter, a neural cell-specific promoter or a viral promoter.

The present invention also provides an implant comprising a population of essentially pure astrocytes. The invention further provides a composition comprising an essentially pure population of astrocytes comprising an exogenous nucleic acid encoding a neuroactive substance.

These and other objects are addressed by this invention, which is explained in greater detail in the attached drawings and the following Detailed Description and Examples.

(A), Phase contrast micrographs showing low magnification (×70) of primary cultures of human adult astrocytes. (B), Higher magnification (×560) of a dividing flat cell at telophasis stage.

FIG. 2: Immunocytochemical characterization of primary cultures of human adult astrocytes.

Low magnification (×280) micrographs illustrating that all the cells were GFAP-(A) and S100β-positive (B).

FIG. 3: In vitro proliferation of human adult astrocytes.

Proliferation rates are expressed as percent of increase in cell number since $t_0$. Human adult astrocytes proliferated in vitro when cultured in FCS. Note that the cells proliferated twice as fast when cultured in the presence of 20% FCS than in 10% FCS (A). NGF and bFGF (50 ng/ml) did not have any mitogenic effects on primary cultured human adult astrocytes (B). Note that when HS was added to the medium, most of the cells did not attach onto the culture dish and they were removed with the medium.

Figure 4A:
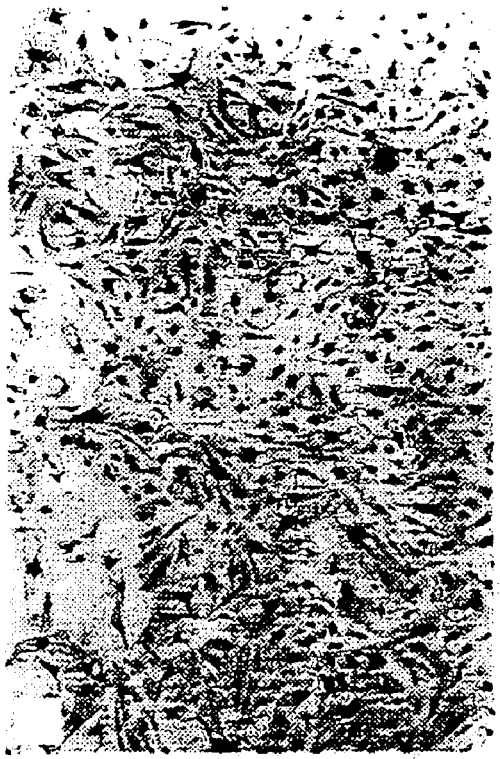
Figure 4B:
Figure 4C:

FIG. 4: TH immunocytochemistry after adenoviral transduction of human adult astrocytes.

(B), Low magnification (×70) micrographs illustrating that 50–60% of the cells were TH-positive one week post-infection (A, non-infected cells). (C), Higher magnification (×560) illustrating transduced astrocytes containing hTH.

Figure 5:
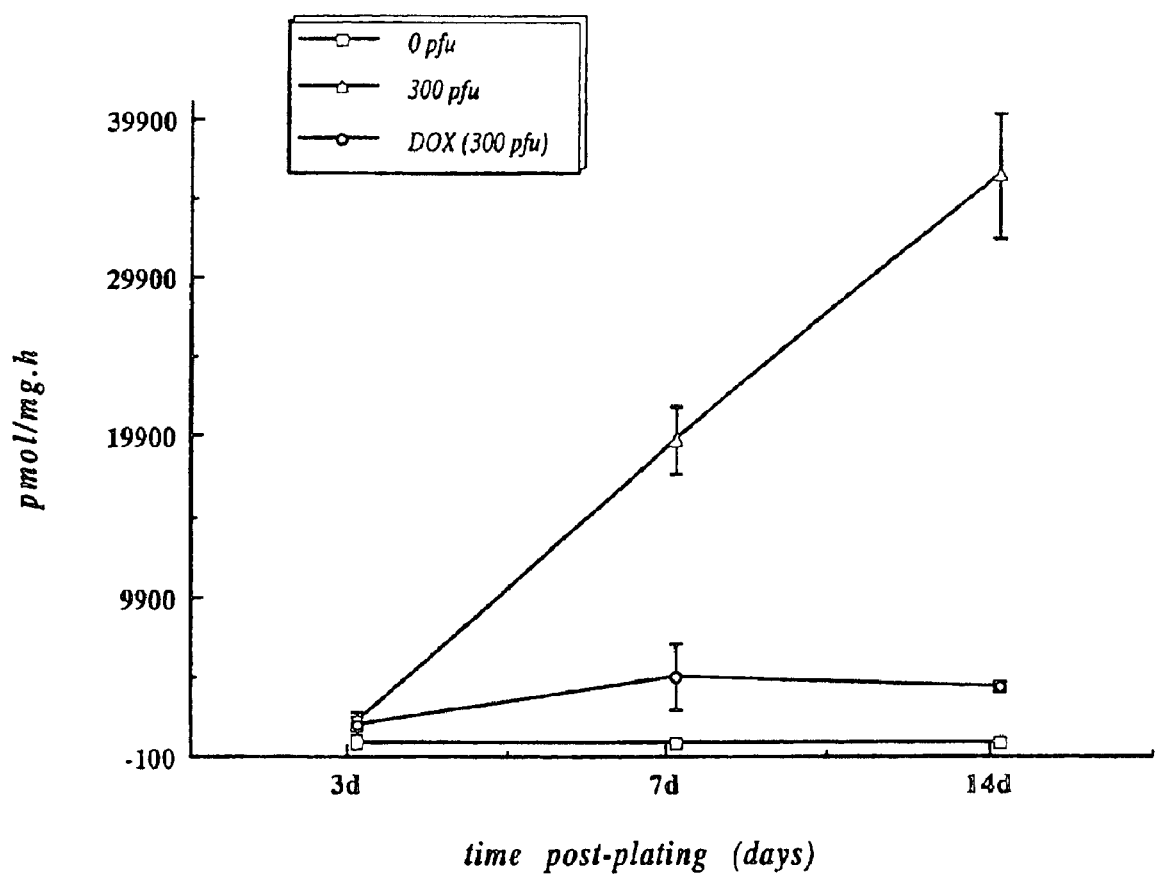

FIG. 5: TH activity in transduced human adult astrocytes

TH activity was detected within the first week post-infection and then increased to 35650 pmol [$^3$H H$_2$O/mg prot./h on day 14. Note that TH activity decreased by at least 10 fold in the presence of doxycycline 14 days post-infection.

DETAILED DESCRIPTION OF THE INVENTION

Definitions

The following defined terms are used throughout the present specification, and should be helpful in understanding the scope and practice of the present invention.

A "polypeptide" is a polymeric compound comprised of covalently linked amino acid residues. Amino acids have the following general structure:

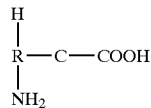

Amino acids are classified into seven groups on the basis of the side chain R: (1) aliphatic side chains, (2) side chains containing a hydrolytic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A "protein" is a polypeptide which plays a structural or functional role in a living cell.

The polypeptides and proteins of the invention may be glycosylated or unglycosylated.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the an.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence. An "exogenous nucleic acid" is genetic material which has been introduced into a cell not naturally containing the nucleic acid sequence.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "vector" is any means for the transfer of a nucleic acid of interest into a host cell. The term "vector" includes both viral and nonviral means for introducing the nucleic acid into a cell in vitro, ex vivo or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors. A nucleic acid may contain one or more regulatory regions, and/or selectable markers useful in selecting, measuring, and monitoring nucleic acid transfer results (transfer to which tissues, duration of expression, etc.).

"Pharmaceutically acceptable carrier" includes diluents and fillers which are pharmaceutically acceptable for methods of administration, are sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

Astrocytes

One aspect of the present invention is to provide a population of essentially pure human astrocyte cells. The purified cells may contain introduced genetic material encoding a product of interest. Another aspect of the instant invention is to provide human adult astrocytes having desired therapeutic properties, and suitable for ex vivo cell therapy. Transplantation of genetically modified human cells to rat brain is disclosed in Sabate et al. (Nature Genetics, Volume 9, pp. 256–260 (1995)), the entire contents of which are incorporated herein by reference.

The present invention now provides a very efficient way to obtain high purity adult human astrocytes, capable of producing factors with biological effect, such as neuroactive substances for ex vivo gene therapy. The inventors have now found conditions that enable successful purification, amplification, and in vitro modification of these cells. Substantial levels of gene expression were obtained in cells modified with a recombinant adenovirus. Genetically modified astrocytes enables gene therapy of neurodegenerative diseases and of trauma to the CNS.

The combination of gene transfer techniques and cell transplantation provides an approach to deliver therapeutic molecules into the CNS. Astrocytes are particularly well suited for CNS therapy because of their CNS origin, their efficient secretory mechanisms and their role as neuronal support. Most importantly, the use of human adult astrocytes as cellular vehicles for ex vivo gene transfer opens the way to autologous transplantation, thus obviating immunological rejection and the side effects of immunosuppressors. As provided herein, these cells can be purified, expanded and genetically modified in vitro. Astrocytes derived from human adult cerebral cortex have been grown and maintained in vitro as pure primary cultures for at least 10 months. In addition, cells are efficiently transduced by viral vectors encoding a neuroactive substance. When the neuroactive substance is human tyrosine hydroxylase (hTH) under the negative control of the tetracycline-based regulatory system (tet-off), the infected cells synthesize large amounts of active hTH and release L-Dopa. In addition, doxycycline, a potent analog of tetracycline, efficiently regulates transgene expression.

Vectors

As discussed above, a "vector" is any means for the transfer of a nucleic acid according to the invention into a host cell. Preferred vectors are viral vectors, such as retroviruses, herpes viruses, adenoviruses, and adeno-associated viruses. Thus, a gene comprising a nucleic acid of interest is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Viral vectors commonly used for in vivo or ex vivo targeting and therapy procedures are DNA-based vectors and retroviral vectors. Methods for constructing and using viral vectors are known in the art [see. e.g., Miller and Rosman, BioTechniques 7:980–990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Defective viruses, which entirely or almost entirely lack viral genes, are preferred. Defective virus is not replication competent after introduction into a cell, and thus does not lead to a productive viral infection. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., Molec. Cell. Neurosci. 2:320–330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [J. Clin. Invest. 90.626–630 (1992); see also La Salle et al., Science 259:988–990 (1993)]; and a defective adeno-associated virus vector [Samulski et al., J. Virol. 61:3096–3101 (1987); Samulski et al., J. Virol. 63:3822–3828 (1989); Lebkowski et al., Mol. Cell. Biol. 8:3988–3996 (1988)].

Preferably, for in vivo administration, an appropriate immunosuppressive treatment is employed in conjunction with the viral vector, e.g., adenovirus vector, to avoid immunodeactivation of the viral vector and transfectecd cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

Naturally, the invention contemplates delivery of a vector to astrocytes that will express a therapeutically effective amount of a gene of interest for gene therapy applications. The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Any vector, viral or non-viral, of the invention will preferably be introduced ex vivo to astrocytes in a pharmaceutically acceptable vehicle or carrier. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Adenovirus Vectors

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94112649 and WO95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 1335, the contents of which are incorporated herein by reference).

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et at., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95102697. Recombinant adenoviruses are recovered and purified using standard molecular biological techniques, which are well known to one of ordinary skill in the art.

Adeno-associated Virus Vectors

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterised. It encompasses approximately 4700 bases and contains an inverted terminal repeat (ITR) region of approximately 145 bases at each end, which serves as an origin of replication for the virus. The remainder of the genome is divided into two essential regions which carry the encapsulation functions: the left-hand pan of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,365; U.S. Pat. No. 5,139,911; EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsulation genes (rep and cap genes), into a cell line which is infected with a human helper virus (for example an adenovirus). The AAV recombinants which are produced are then purified by standard techniques.

The invention also relates, therefore, to an AAV-derived recombinant virus whose genome encompasses a sequence encoding a nucleic acid of interest flanked by the AAV ITRs. The invention also relates to a plasmid encompassing a sequence encoding a nucleic acid encoding an anti-angiogenic factor flanked by two ITRs from an AAV. Such a plasmid can be used as it is for transferring the nucleic acid sequence, with the plasmid, where appropriate, being incorporated into a liposomal vector (pseudo-virus).

Retrovirus Vectors

In another embodiment the gene can be introduced in a retroviral vector, e.g., as described in Anderson et al., U.S. Pat. No. 5,399,346: Mann et al., 1983. Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.: and Kuo et al., 1993, Blood 82:845. The retroviruses are integrating viruses which infect dividing cells. The retrovirus genome includes two LTRs, an encapsulation sequence and three coding regions (gag, pol and env). In recombinant retroviral vectors, the gag, pol and env, genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsulation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsulation sequences which may include a part of the gag gene (Bender et al., J. Virol. 61 (1987) 1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Targeted gene delivery is described in International Patent Publication WO 95/28494, published October 1995.

Non-viral Vectors

Alternatively, the vector can be introduced to astrocytes by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey. et al., *Proc. Natl. Acad. Sci. U.S.A.* 85:8027–8031 (1988); Ulmer et al., *Science* 259:1745–1748 (1993)]. The use of cationic lipids may promote encapsulation of negatively charged nucleic acids, and also promote fusion with negatively charged cell membranes [Feigner and Ringold, *Science* 337:387–388 (1989)]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into specific cells ex vivo has certain practical advantages. Molecular targeting of liposomes to specific cells represents one area of benefit. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

Other molecules are also useful for facilitating transfection of a nucleic acid, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990; Williams et al., *Proc. Natl. Acad. Sci. USA* 88:2726–2730 (1991)]. Receptor-mediated DNA delivery approaches can also be sued [Curiel et al., *Hum. Gene Ther.* 3:147–154 (1992); Wu and Wu, *J. Biol. Chem.* 262:4429–4432 (1987)].

Nucleic Acids

Genetic modification and grafting of astrocytes enables their use in numerous applications, depending on the introduced genetic material.

Reporter genes, such as the Lac Z gene, may help to solve important scientific questions in the field of neural development. In particular, the potential of progenitors explanted from various zones of the brain to survive and differentiate idependently of their origin could be investigated by following them after grafting in various zones of developing or adult brains.

Nucleic acids comprising a therapeutic gene are of particular interest. These genes include any gene encoding a neuroactive substance; a substance capable of exerting a beneficial effect on cells of the central nervous system. It may be a substance capable of compensating for a deficiency in or of reducing an excess of an endogenous substance. Alternatively, it may be a substance conferring new properties on the cells.

The neuroactive substance may be an antisense sequence, a polypeptide or a protein. Among the polypeptides and proteins suitable for practice of the invention are growth factors, neurocrophic factors, cytokines, neurotransmitters, enzymes, neurotransmitter receptors and hormone receptors.

Preferably, the growth factor is a colony stimulating factor (G-CSF, GM-CSF, M-CSF, CSF, and the like), endothelial cell growth factor (ECGF, FGF1), fibroblast growth factor (aFGFa, bFGF) or vascular cell growth factor (VEGF). Among the neurotrophic factors, the preferred factors are ciliary neurotrophic factor (CNTF), glial cell maturation factors (GMFa, b), GDNF, BDNF, NT-3, NT-5 and the like. The complete nucleotide sequence encoding NT-3 is disclosed in WO91/03569, the contents of which are incorporated herein by reference.

Preferred cytokines are the interleukins and interferons. Enzymes included within the scope of the invention are the enzymes for the biosynthesis of neurotransmitters (tyrosine hydroxylase, acetylcholine transferase, glutamic acid decarboxylase) and the lysosomal enzymes (hexosaminidases, arylsulphatase, glucocerebrosidase, HGPRT). The enzymes involved in the detoxification of free radicals (super oxide dismutase I, II or III, catalase, glutathione peroxidase) are preferred. Receptors include the androgen receptors (involved in Kennedy's disease).

These proteins may be used in native form, or in the form of a variant or fragment thereof.

The neuroactive substance may also be an antisense sequence. The down regulation of gene expression using antisense nucleic acids can be achieved at the translational or transcriptional level. Antisense nucleic acids of the invention are preferably nucleic acid fragments capable of specifically hybridizing with a nucleic acid encoding an endogenous neuroactive substance or the corresponding messenger RNA. These antisense nucleic acids can be synthetic oligonucleotides, optionally modified to improve their stability and selectivity. They can also be DNA sequences whose expression in the cell produces RNA complementary to all or part of the mRNA encoding an endogenous neuroactive substance. Antisense nucleic acids can be prepared by expression of all or part of a nucleic acid encoding an endogenous neuroactive substance, in the opposite orientation, as described in EP 140308. Any length of antisense sequence is suitable for practice of the invention so long as it is capable of down-regulating or blocking expression of the endogenous neuroactive substance. Preferably, the antisense sequence is at least 20 nucleotides in length. The preparation and use of antisense nucleic acids, DNA encoding antisense RNAs and the use of oligo and genetic antisense is disclosed in WO92/15680, the contents of which are incorporated herein by reference.

The nucleic acid may be of natural or artificial origin. It may be especially genomic DNA (gDNA), complementary DNA (cDNA), hybrid sequences or synthetic or semisynthetic sequences. It may be of human, animal, plant, bacterial or viral origin and the like. It may be obtained by any technique known to persons skilled in the art, and especially by screening libraries, by chemical synthesis, or alternatively by mixed methods including chemical or enzymatic modification of sequences obtained by screening libraries. It is preferably cDNA or gDNA.

More preferred therapeutic products include in the case of Parkinson's disease the cDNA encoding tyrosine hydroxylase (TH) or a neurotrophic factor such as BDNF (brain derived neurotrophic factor) which favor the survival of dopaminergic neurons.

Similarly, for Alzheimer's disease, the cDNA encoding choline acetyl transferase and/or NGF (nerve growth factor) could prevent degeneration of cholinergic neurons.

Recent findings suggest that neurotrophic factors like BDNF and GDNF can be trophic factors for dopaminergic cells. Introduction into astrocytes of genetic material encoding neurotrophic factors are expected to improve graft survival.

Several adenovirus vectors encoding therapeutic genes have now been constructed. For instance, an adenovirus encoding tyrosine hydroxylase (TH) has been constructed. The grafting of in vitro infected astrocytes according to the invention constitutes a very efficient way to deliver therapeutic amounts of TH in the brain. Other a adenovirus-derived vectors encoding therapeutic genes include Ad-aFGF, Ad-bFGF, Ad-GDNF, Ad-GAD.

The genetic material of interest can also be an antisense-RNA or ribozyme or a DNA molecule encoding said antisense-RNA or ribozyme. These products are of particular interest for inhibiting production of toxic proteins such as β-amyloid precursor, TAU proteins. etc.

Preferably, the genetic material is a DNA encoding a protein or peptide of interest. As indicated above, said protein or peptide is preferably a neuroactive substance such as a growth factor (i.e. a cytokine) a neurotrophic factor, an enzyme or a neurotransmitter.

In an other embodiment, the genetic material is a DNA encoding an antisense-RNA or a ribozyme Regulatory Regions Generally, the nucleic acids of the present invention are linked to one or more regulatory regions. Said regions can include a regulatable or inducible promoter; neural cell-specific promoter, or viral promoter. Selection of the appropriate regulatory region or regions is a routine matter, within the level of ordinary skill in the art.

The regulatory regions may comprise a promoter region for functional transcription in astrocytes, as well as a region situated in 3' of the gene of interest, and which specifies a signal for termination of transcription and a polyadenylation site. All these elements constitute an expression cassette.

Promoters that may be used in the present invention include both constituitive promoters and regulated (inducible) promoters. The promoter may be naturally responsible for the expression of the nucleic acid. It may also be from a heterologous source. In particular, it may be promoter sequences of eucaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the adenovirus E1A or major late promoter (MLP), a cytomegalovirus (CMV) promoter or a Rous Sarcoma Virus (RSV) promoter.

In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted, such as into the virus genome downstream of such a sequence.

Some promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV40, E1a, and MLP promoters. Tetracycline-regulated transcriptional modulators and CMV promoters are described in WO 96/01313, U.S. Pat. Nos. 5,168,062 and 5,385,839, the contents of which are incorporated herein by reference.

Pharmaceutical Administration

The present invention enables purification and amplification of adult human astrocytes, and their use for the successful delivery of genes in vitro with high efficiency. These cells can then be administered to the CNS of recipient organisms. The invention thereby provides important clinical and scientific applications, such as treatment of trauma to the CNS and of neurodegenerative disorders.

The process according to the present invention enables one to target precisely a particular region of the CNS, such as a site within the brain, depending on the transferred therapeutic gene and the disorder to be treated. Thus, according to the site of the impairment to be treated, the administration is made into sites of the brain including, for instance, the striatum, hippocampus or substantia nigra. Preferably, they are grafted in the striatum.

According to the present invention, it is now possible, by stereotactic injection, to deliver astrocytes for engraftment. Determination of the coordinates for administration would be based on the disorder to be treated, and would be determined by the skilled practitioner. The actual therapeutic regimen, including site of injection(s), number and schedule of injections, and particular dosage(s), would also be determined by the skilled practioner. In general, the number of cells engrafted at a site will be between $1 \times 10^3$ and $1 \times 10^{10}$, preferably $1 \times 10^5$ to $1 \times 10^9$, and more preferably $1 \times 10^5$, to $1 \times 10^9$.

It is also an object of the invention to provide an implant comprising astrocyte cells as described above. Preferably, the implant contains non-cellular material increasing survival and in vivo proliferation and differenciation of the cells. The implant can contain for instance collagen, gelatin, fibronectin, lectins, bio-compatible supports such as bone or polytetrafluoroethylen fibers, etc). The invention also concerns a method for the delivery of a therapeutic product to the CNS of a recipient comprising grafting into the brain of said recipient genetically-modified human astrocytes containing introduced genetic material encoding said therapeutic product.

The invention provides safe, non toxic, long term expression of therapeutic genes in vivo. The invention is of particular interest in the treatment of neurodegenerative disorders such as neuropathies, strokes, spinal cord injury, amyotrophic lateral sclerosis, Huntington's chorea, Alzheimer's and Parkinson's diseases, cerebral palsy, epilepsy, lysosomal diseases (e.g. Tay Sachs and Sandhoff diseases, metachromatic leucodystrophy, Gaucher's disease, mucopolysaccharidosis, Lesh Nyhan, etc) as well as brain tumours.

The present invention may be better understood by reference to the following non-limiting Examples, which are provided as exemplary of the invention.

EXAMPLES

The present invention will be described in greater detail with the aid of the following examples which should be considered as illustrative and non-limiting. Example 1 describes a cell culture protocol enabling the recovery of long-term, pure primary cultures of human adult astrocytes. Example 2 demonstrates that these cells can be genetically modified by using an adenoviral vector encoding human tyrosine hydroxylase (TH) under the control of the tetracycline-based (tet-off) regulatory system (Gossen and Bujard, 1992). TH is the rate limiting enzyme for the synthesis of catecholamines, by converting tyrosine to L-Dopa. Several studies have demonstrated its therapeutic potential in animal model of Parkinson's disease (Wolff et al., 1989; Horellou et al., 1990a,b; Fisher et al., 1991). Infected cells produced large amounts of active hTH in the absence of doxycycline, a potent analog of tetracycline.

General Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory, Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Example 1

Explantation and Characterization of Primary Cultured Human Adult Astrocytes 1.1 Cell Culture Adult human tissue was isolated from the cerebral cortex of patients (average age 51.5±16.8 years old) undergoing surgical resections, with the consent of the patient, according to the policy of the hospital. Immediately after surgery, the tissue was mechanically dissociated and centrifuged in DMEM/F12 (Sigma) containing D-glucose (3.15 g/l), HEPES (3.57 g/l), sodium bicarbonate (1.2 g/l), and supplemented with 10% fetal calf serum (FCS, Seromed), 2 mM glutamine (Gibco), antibiotics (penicillin/streptomycin mix, 100 µg/ml, Gibco) and fungizone (Gibco), pH 7.4. The pellet was resuspended in the same medium and plated in a 5 cm culture flask (Costar). Cultures were maintained at 37° C. in a humidified atmosphere containing 10% $CO_2$. Forty-eight hours later, the medium was changed. These primary cultures were maintained by changing the medium once a week thereafter.

As freezing/thawing procedures, confluent cells were harvested with 0.25% trypsin and 0.2% EDTA (Gibco) and rapidly washed with phosphate buffered saline (PBS, 0.1 M, pH 7.4) to remove the medium-containing serum. The cells were then frozen first at −20° C. and finally stored at −80° C. in DMEM/F12 supplemented with 10% dimethylsulfoxide (DMSO, Sigma). Cells were thawed by placing the vial in a water bath at 40° C. for 2–4 minutes, and replated in a Costa culture flask. Forty-eight hours later, the medium was replaced to eliminate DMSO.

1.2 Assessment of Cell Proliferation

Two different methods were used: direct counting under phase-contrast in a predetermined area of 2 $mm^2$ and GFAP-bromodeoxyuridine labeling (BrdU, an analog of thymidine which is only incorporated into replicating DNA) revealed with a double immunofluorescence protocol. Primary cultured cells were plated onto NUNC™ Petri dishes (60×15 mm) with grids (2 mm$^2$) in DMEM/F12.

The proliferation rate was determined under various culture conditions: (a) without FCS, (b) with 10% FCS, (b) 20% FCS, (c) 10% FCS and 5% horse serum (HS), (d) 10% FCS and 10% HS, (e) NGF (50 ng/ml, Sigma), (f) bFGF (50 ng/ml, Boehringer-Mannheim). For proliferation experiments, the medium was changed twice a week. All cultures were counted every 10 hours for 80 hours. The activity of the NGF and bFGF used was ascertained by bioassay: the neuritic extension of PC12 cells (cultured on polyomithine-coated dishes in RPMI supplemented with 10% HS and 5% FCS) exposed to NGF (50 ng/ml), and the differentiation of neuroepithelial progenitor cells in the presence of bFGF (10 ng/ml in DMEM/HAMF12 (see refs in Sabate et al., 1995).

For BrdU incorporation experiments, BrdU was added to primary cultures 2 days post-plating. Cultures were incubated in the presence of 5 or 10 μM BrdU for 4 days. The BrdU treatment was performed simultaneously on 3T3 and 293 cells as proliferation controls. The positive cells were detected by immunocytochemistry, as indicated below.

1.3 Immunocytochemical Procedures

Cells in primary cultures were rapidly rinsed in PBS, incubated in a fixative solution (4% paraformaldehyde in PBS) for 10 min at room temperature. After rinses in PBS, the cells were treated with a blocking solution (10% goat serum and 0.2% Triton X-100 in PBS) for 30 min at room temperature, and then incubated with the primary polyclonal antibody (GFAP, Dakopatts, 1:100; S100β, Sigma, diluted 1:100; TH, Inst. J. Boy, diluted 1:200; BrdU, Jackson, 1:50; OX42, Cedarlane, 1:200) containing 5% goat serum and 0.1% Triton X-100 in PBS.

For BrdU immunodetection, the cells were first denatured in 2N HCl for 20 min, at room temperature. After neutralization in 0.1N sodium borate for 10 min, the samples were rinsed in PBS and processed as described for GFAP immunocytochemistry.

1.4 Characterization of Cultured Astrocytes

To assess the potential of human adult astrocytes for autologous transplantation into the CNS, it was first necessary to test whether these cells can be maintained as primary cultures. Previous studies reported that primary cultures of human adult astrocytes were enriched in microglial cells (Yong et al., 1991, 1992). The composition of the medium and the times between tissue resection, dissociation and cell seeding were varied in order to optimize the culture procedures to obtain astrocyte-enriched preparations. DMEM supplemented with serum is an appropriate culture medium for rodent astroglial cultures. Enriched DMEM supplemented with fetal calf serum (FCS) and with HAM/F12 nutrients was used for astrocyte cultures. The first cells to attach to the culture dish after dissociation and seeding are astrocytes. Various lag times (24–120 hours) until the first change of medium containing unattached and/or dead cells and cell debris were tested. A 48 hour (2 days) delay was optimal for obtaining essentially pure astroglial cultures. Surprisingly, microglial cells do not attach to the culture dish under these conditions.

Figure 1A:
FIG. 1: Primary culture from human adult cerebral cortex.
Figure 1B:
Figures 2A, 2B:
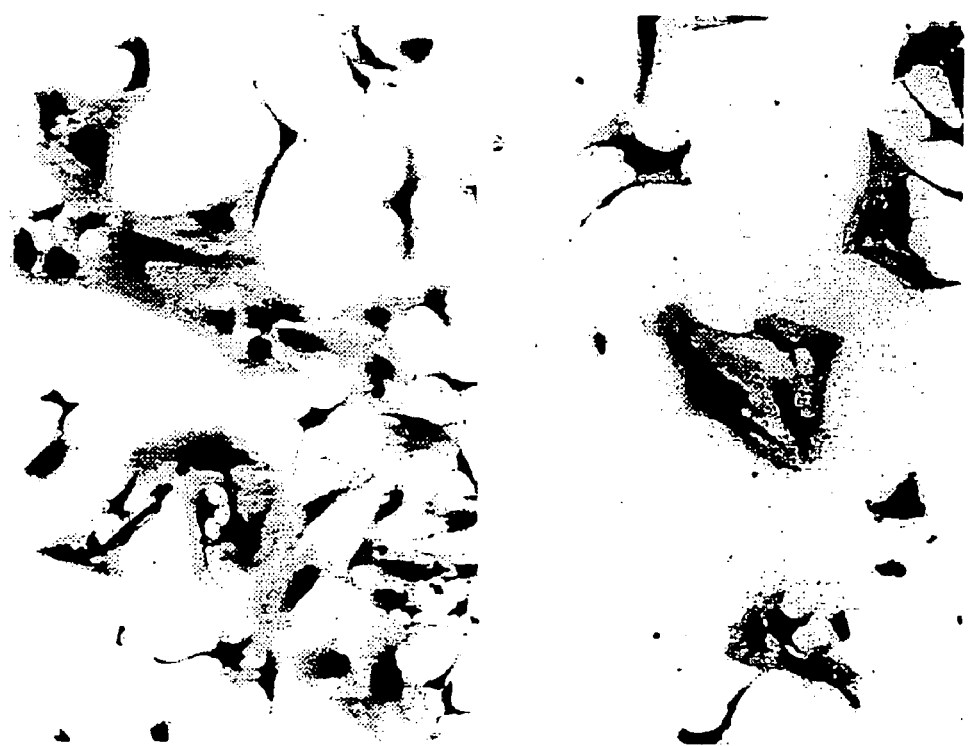

After two days in DMEM/F12 supplemented with 10% FCS, cells were flattened in the culture dish. Although cell morphology depended on culture confluence, the large majority of cells exhibited a flat polygonal morphology (FIGS. 1A–B). The flattened cells were identified by immunodetection of astroglial markers including GFAP, the major gliofilament protein, and S100β, a cytoplasmic calcium-binding protein (FIG. 2). Virtually all the primary cultured cells were GFAP- (FIG. 2A) and S100β-positive (FIG. 2B). The presence of microglial cells in the cultures was tested by OX42 immunostaining and labeling with B$_4$ isolectin from *Griffonia simplicifolia*, which is used as a specific marker for microglial cells (Streit, 1990). No staining was observed, confirming the presence of a culture of astrocytes essentially free of microglial cells. Taken together, these results show that the present invention provides an essentially pure culture of human adult astrocytes. Microscopic inspection of the cultures revealed that many GFAP-positive cells were in mitosis (FIG. 1B).

1.4.1 In Vitro Proliferation of Human Adult Astrocytes

Figure 3A:
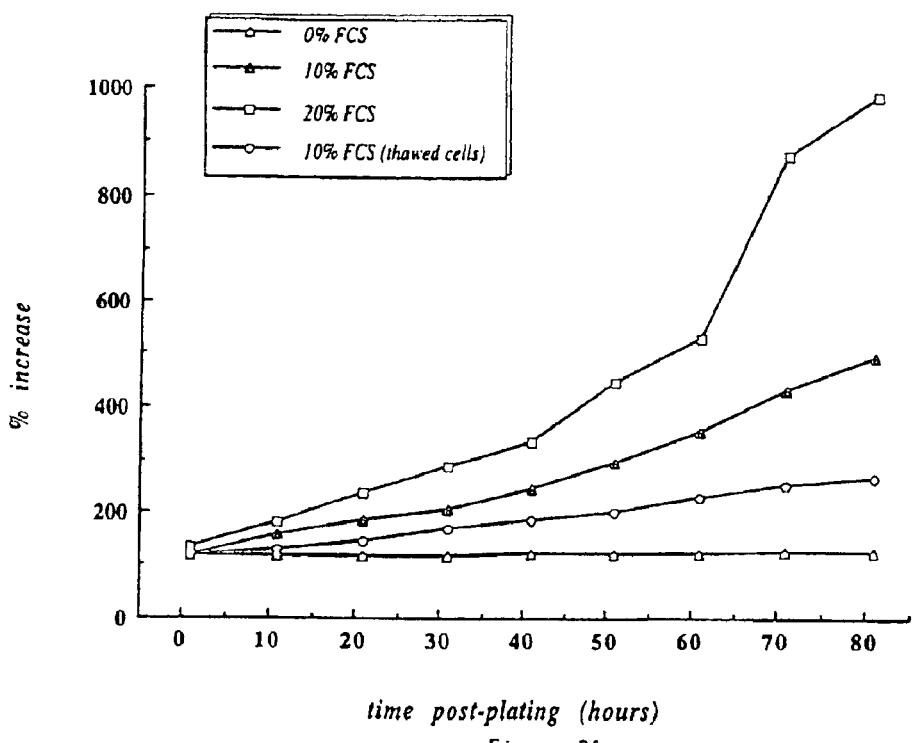
Figure 3B:
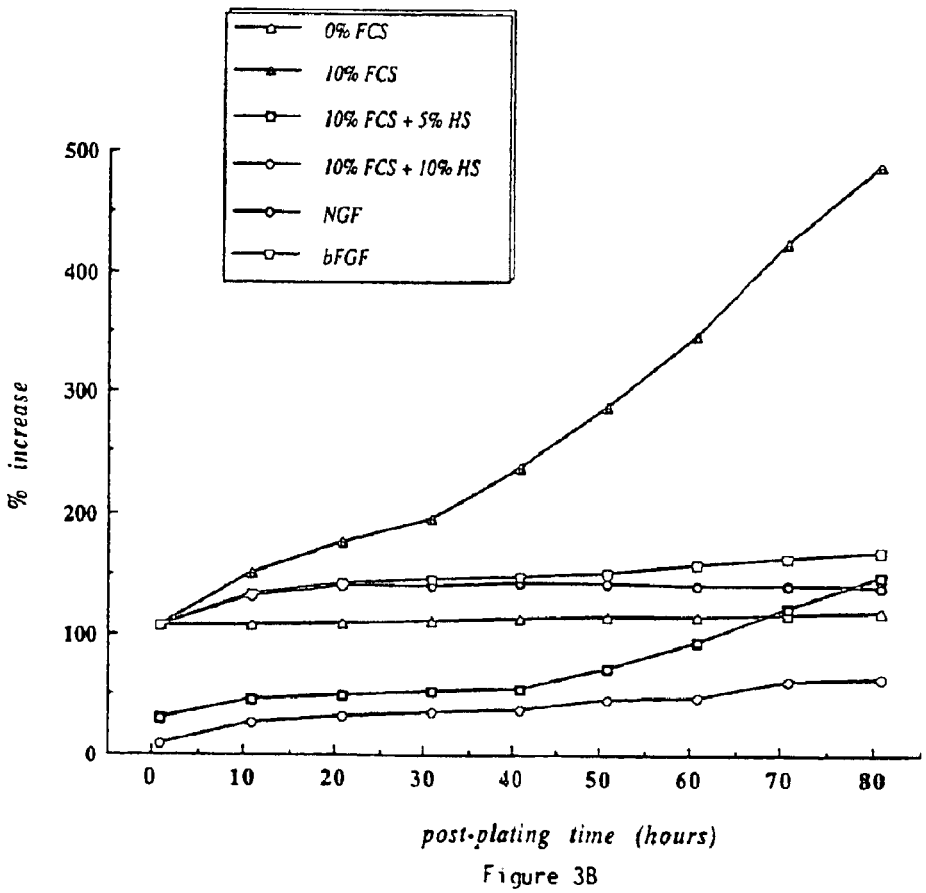

Preliminary observations indicated that without FCS, none or few of the cultured cells were dividing, whereas mitotic profiles were often observed when 10% FCS was added to the DMEMF12 medium. Double immunofluorescent labeling of GFAP and BrdU revealed that the dividing cells were astrocytes. The capacity of primary cultured human adult astrocytes to proliferate in various culture conditions was analyzed. Soluble molecules including the trophic factors NGF and bFGF, and serum of various species have mitogenic properties on cultured rodent and human fetal astrocytes (see refs in Yong et al., 1991, 1992, and Stachowiak et al., 1997). The effects of various combinations, including FCS, HS, bFGF and NGF, on cell proliferation was tested: 0, 10 and 20% FCS, 10% FCS supplemented with 5 or 10% HS, DMEM supplemented with 50 ng/ml bFGF, DMEM supplemented with 50 ng/ml NGF (FIGS. 3A–B). Twelve hours after seeding in the presence of FCS, the cells attached and flattened onto the dish surface. Cells only proliferated in tile presence of FCS (FIG. 3A), and proliferation was maximum at 20% FCS. When cultured in the presence of 10% or 20% FCS, the astroglial population doubled in 40 hours and 20 hours respectively (FIG. 3A). The rate of cell proliferation in the presence of 20% FCS is suitable for cell transplantation, enabling the recovery of 1–5×10$^6$ human adult astrocytes within one month from a single biopsy.

Surprisingly, the addition of NGF or bFGF (50 ng/ml medium) did not accelerate the proliferation of human adult astrocytes (FIG. 3B). When cultured with FCS supplemented with 5 or 10% HS, most of the human adult astrocytes did not attach to the culture dish and remained in the medium. Nevertheless, a few spherical cells attached but did not flatten onto the culture dish. From 3 days post-plating, some of the attached cells flattened and proliferated very slowly (FIG. 3B). In summary, human adult astrocytes can be expanded in vitro in the presence of FCS. Twenty percent FCS enables the recovery of a large number of cells suitable for cell transplantation.

1.4.2 Cell Characterization Following Freezing/thawing Procedures

A patient may receive more than one transplant. Therefore, one issue in the development of autologous grafting in humans is the cryopreservation of primary cultured astrocytes from a single biopsy. Human adult astroglial cells were tested for grwoth after freezing/thawing procedures. At the first passage, corresponding to 3–4 weeks in vitro in DMEM/F12 supplemented with 10% FCS, cultured cells were frozen and kept at −80° C. for 2–6 months. Then, cells were rapidly thawed and seeded in DMEM/F12 supplemented with 10% FCS. Cells were carefully observed daily. Ten hours after thawing and seeding, the cells attached and flattened onto the culture dish. They exhibited similar morphological and immunocytochemical features as cells which had not been subjected to freezing procedures. GFAP and S100β immunostaining confirmed that these cells conserved their astroglial phenotype. During the first day post-plating, the cells did not proliferate. Between day 2 and day 3, the first mitotic profiles were observed. Then, the cell expansion accelerated, and the mean division time was 60 hours in the presence of 10% FCS (FIG. 3A). Therefore, human adult astrocytes obtained according to the present invention maintain their capacity to divide following freezing/thawing procedures.

Example 2

Genetic Modification of Cultured Astrocytes 2.1. Adenoviral Vectors

Adenoviral vectors represent efficient tools to transfer foreign genes to nerve cells as shown by recent studies where direct intracerebral injection to rodent brain provides gene therapy of the central nervous system (WO94/08026). In order to amplify the number of cells suitable for grafting, the inventors have demonstrated that recombinant adenoviruses can efficiently allow gene transfer to cultured human astrocytes.

Many Adenovirus-derived vectors have been disclosed in the literature and can be prepared by one skilled in the art. Such vectors can be used in the present invention. (see in particular EP 185 573, Perricaudet et al., FEBS Letters 267 (1990) 60; Levrero et al, Gene 101 (1991) 195, FR 9305954, FR9308596, WO94/12649). An Ad.RSVβgal vector has previously been disclosed in the literature. See for example Stratford-Perricaudet et al. (*J.Clin.Invest*. 90, 626–630 (1992)). This vector contains the *E.coli* LacZ gene inserted in an adenovirus Ad5 deleted for the E1 and E3 regions.

2.2 Infection of Human Adult Astrocytes with AdPGKtet hTH-1

Cells were seeded on 6 well culture plates at a density of $6 \times 10^4$ cells/well in DMEM/F12 without serum (FCS). Then, the cells were incubated for 4–6 hours with AdPGKtet hTH-1, in which a human tyrosine hydroxylase gene (hTH-1) is under the control of the tetracycline-based "tet-off" regulatory system (Gossen and Bujard, 1992). The hTH gene and the transactivator are driven respectively by a minimal CMV and phosphoglycerate kinase (PGK) promoter. Different multiplicities of infection (MOI) were tested (75, 150 and 300 pfu/cells). Doxycycline was added to the culture medium to a final concentration of 10 ng/ml. The medium was renewed every second day.

2.3 Assessment of TH Activity and L-Dopa Production by Transduced Human Adult Astrocytes Three, 7 and 14 days after infection, cells were harvested and processed to measure TH activity and evaluate L-Dopa production. TH activity of cell pellets was assayed as previously described (Reinhard et al. 1986). The production of L-Dopa was assessed after growing human astrocytes for 24 h in DMEM/F12 without FCS. Conditioned media was collected, and 0.5 ml aliquots were mixed with an alumina suspension (40 mg/ml) in 0.05 M Tris-HCl, pH 8.6. Each mixture was then continuously stirred for 10 min, washed with the Tris-HCl buffer, and the alumina finally collected by centrifugation (800 g, 5 min. 4° C.). Catechols adsorbed onto the alumina gel were eluted with 0.6 N perchloric acid (0.1 ml per sample), and the eluate was neutralized with 2 M potassium phosphate pH 7.4 (20 µl per sample). After centrifugation (30 000 g, 15 min, 4° C.), 10 µl aliquots of the cleared supernatant were injected into a high performance liquid chromatography column (Ultrasphere IP, 25 cm, 0.46 cm outer diameter, 5 µm) for the electrochemical quantification of L-Dopa, as described in detail elsewhere (Adrien et al., 1989).

2.4 Result of Genetic Engineering of Human Adult Astrocytes

Cultured human adult astrocytes can be modified by a recombinant adenoviral vector. Optimal transduction is obtained by infecting the cells with a viral preparation of 300 pfu/cell for 6 hours. No obvious toxicity was observed. Fifty-60% of the cells were hTH-positive as assessed by immunocytochemistry (FIGS. 3A–B). An enzymatic assay developed by Reinhard and colleagues (1986) was used to test whether the hTH was active 3, 7 and 14 days post-infection. TH activity was detectable 3 days after infection he (1,290 pmol/mg prot/h), and higher on days 7 (19,000 pmol/mg prot/h) and 14 (35,650 pmol/mg prot/h). In addition, HPLC assays showed that TH-transduced human astrocytes produced 1 µg L-Dopa /$10^6$ cells/24 h, 14 days-post-infection.

To test the efficacy of the tetracycline-based regulatory system, the astroglial cultures were treated with doxycycline (10 ng/ml), a potent analog of tetracycline. Doxycycline efficiently reduced TH expression. TH activity was decreased by at least 10 fold in the presence of doxycycline on day 14 (3,590 pmol/mg prot/h in doxycycline-treated cells vs 35,650 pmol/mg prot/h in untreated cultures) (FIG. 4). This indicated that the hTH-1 expression was efficiently controlled by doxycycline. However, as shown on FIG. 4, in doxycycline-treated astrocytes, the level of TH activity did not return to baseline. This observation suggested that the minimal promoter P*hCMV, which drives the expression of hTH-1 in the AdPGKtet hTH-1vector, has a basal activity in the primary cultured human adult astrocytes. Indeed, previous studies report activation of a hCMV promoter in astrocytes under certain experimental conditions, such as after injury, suggesting a environmental regulation of hCMV promoter (McCarthy et al., 1995, Fritschy et al., 1996).

2.5 Use of Other Vectors

As indicated above, other types of vectors can be used to genetically modify the astrocytes according to the invention. This can be viral or non-viral (chemical) vectors. Preferred viral vectors include AAV, retroviruses, herpes viruses and vaccinia virus. Non viral vectors include Calcium-phosphate precipitation, liposome-mediated transfection, cationic lipid transfection and lipopolyamine-mediated transfection.

All the references discussed herein are incorporated by reference.

One skilled in the art will readily appreciate the present invention is well adapted to carry out the objects and obtain the ends and advantages mentioned, as well as those inherent therein. The peptides, polynucleotides, methods, procedures and techniques described herein are presented as representative of the preferred embodiments, and intended to be exemplary and not intended as limitations on the scope of the present invention. Changes therein and other uses will occur to those of skill in the art which are encompassed within the spirit of the invention or defined by the scope of the appended claims.

References

ADRIEN. J., LANFUMEY, L., GOZLAN, H., FATTACCINI. C. M., and HAMON, M. (1989). Biochemical and electrophysiological evidence for an agonist action of CM 57493 at pre- and post-synaptic 5-HT$_{1A}$ receptors in brain. J. Pharmacol. Exp. Ther. 248, 1222–1230.

ALOISI, F., BORSELLINO, G., SAMOGGIA, P., TESTA, U., CHELUCCI, C., RUSSO, G., PESCHLE, C. LEVI, G. (1992). Astrocyte cultures from human embryonic brain: characterization and modulation of surface molecules by inflammatory cytokines. J. Neurosci. Res. 32, 494–506.

AUBERT, I., RIDET, J. L., and GAGE, F. H. (1995). Regeneration in the adult mammalian CNS: guided by development. Curr. Opin. Neurobiol. 5, 625–635.

BILANG-BLEUEL, A., REVAH, F., COLIN, P., LOCQUET, I., ROBERT, J. J., MALLET, J. and HORELLOU, P. (1997). Intrastriatal injection of an adenoviral vector expressing GDNF prevents dopaminergic neuron degeneration and behavioral impairment in a rat model of Parkinson's disease. Proc. Natl. Acad. Sci. USA 94, 8818–8823.

CASTILLO Jr., B., DEL CERRO, M., BREAKFIELD, X. O., FRIM, D. M., BARNSTABLE, C. J., DEAN, D. O., and BOHN, M. C. (1994). Retinal ganglion cell survival is promoted by genetically modified astrocytes designed to secrete brain-derived neurotrophic factor (BDNF). Brain Res. 647, 30–37.

CORTI, O., HORELLOU, P., COLIN, P., CATTANEO, E., and MALLET, J. (1996). Intracerebral tetracycline-dependent regulation of gene expression in grafts of neural precursors. NeuroReport 7, 1655–1659.

CUNNINGHAM, L. A., HANSEN, J. T, SHORT, M. P., and BOHN, M. C. (1991). The use of genetically altered astrocytes to provide nerve growth factor (NGF) to adrenal chromaffin cell grated into the striatum. Brain Res. 561, 192–202.

CUNNINGHAM, L. A., SHORT, M. P., BREAKFIELD, X. O., and BOHN, M. C. (1994). Nerve growth factor released by transgenic astrocytes enhanced the function of adrenal chromaffin cell grafts in a rat model of Parkinson's disease. Brain Res. 558, 219–223.

FISHER, L. J., and GAGE, F. H. (1993). Grafting in the mammalian central nervous system. Physiol. Rev. 73, 583–616.

FISHER, L. J. (1997). Neural precursor cells: applications for the study and repair of the central nervous system. Neurobiol. Dis. 4, 1–22.

FISHER, L. J., JINNAH, H. A., KALE, L. C., HIGGINS, G. A., and GAGE, F. H. (1991). Survival and function of intrastriatally grafted fibroblasts genetically modified to produce L-DOPA. Neuron 6, 371–380.

FRITSCHY, J. M., BRANDNER, S., AGUZZI, A., KOEDOOD, M., LUSCHER, B., and MITCHELL, P. J. (1996). Brain cell type specificity and gliosis-induced activation of the human cytomegalovirus immediate-early promoter in transgenic mice. J. Neurosci. 16, 2275–82.

GAGE, F. H., RAY, J., and FISHER, L. J. (1995). Isolation, characterization and use of stem cells from the CNS. Ann. Rev. Neurosci. 18, 159–192.

GOODMAN, J. C., TRASK, T. W., CHEN, S. H., WOO, S. L. C, GROSSMAN, R. G., CAREY, K. D., HUBBARD, G. B., CARRIER, D. A., RAJAGOPALAN, S., AGUILAR-CORDOVA, E., and SHINE, H. D. (1996). Adenoviral-mediated thymidine kinase gene transfer into the primate brain followed by systemic ganciclovir; pathologic, radiologic, and molecular studies. Human Gene Ther. 7, 1241–1250.

GOSSEN, M., and BUJARD, H. (1992). Tight control of gene expression in mammalian cells by tetracycline-responsive promoters. Proc. Natl. Acad. Sci. USA 89, 5547–5551.

GOSSEN, M., FREUNDLIEB, S., BENDER, G., MULLER, G., HILLEN, W., and BUJARD, H. (1995). Transcriptional activation by tetracyclines in mammalian cells. Science 268, 1766–1769.

HORELLOU, P., BRUNDIN, P., KALEN, P., MALLET, J., and BJÖRYLUND, A. (1990a). In vivo release of DOPA and dopamine from genetically engineered cells grafted to the denervated striatum. Neuron 5, 393–402.

HORELLOU, P., MARLIER, L., PRIVAT, A., and MALLET, J. (1990b). Behavioral effect of engineered cells that synthesize L-Dopa or dopamine after grafting into the rat neostriatum. Eur. J. Neurosci. 2, 116–119.

HORELLOU, P., VIGNE, E., CASTEL, M. N., BARNEOUD, P., COLIN, P., PERRICAUDET. M., DELAERE, P. and MALLET, J. (1994). Direct intracerebral gene transfer of an adenoviral vector expressing tyrosine hydroxylase in a rat model of Parkinson's disease. NeuroReport 6, 49–53.

JUORIO, A. V., LI, X. M., WALZ, W., and PATERSON, I. A. (1993). Decarboxylation of L-dopa by cultured mouse astrocytes. Brain Res. 626, 306–309.

KISTNER, A., GOSSEN, M., ZIMMERMANN, F., JERECIC J., ULLMER, C., LUBBERT, H., and BUJARD, H. (1996). Doxycycline-mediated quantitative and tissue-specific control of gene expression in transgenic mice. Proc. Natl. Acad. Sci. USA 93, 10933–10938.

KOJIMA, H., ABIRU, Y., SAKAJIRI. K., WATABE, K., OHISHI, N., TAKAMORI, M., HATANAKA, H., and YAGI, K. (1997). Adenovirus-mediated transduction with human glial cell line-derived neurotrophic factor gene prevents 1-methyl-4-phenyl-1,2,3,6-tetrahydropyridine-induced dopamine depletion in striatum of mouse brain. Biochem. Biophys. Res. Commun. 238, 569–573.

LA GAMMA, E. F., WIESINGER, G., LENN, N. J., and STRECKER, R. E. (1993). Genetically modified primary astrocytes as cellular vehicles for gene therapy in the brain. Cell Transplant. 2, 207–214.

LEVALLOIS, C., MALLET, J., and PRIVAT, A. (1996). An adenovirus vector encoding tyrosine hydroxylase activity may enter human CNS cells in primary dissociated cultures. Int. J. Dev. Neurosci. 14, 613–619.

LIN, Q., CUNNINGHAM, L. A., EPSTEIN, L. G., PECHAN, P. A., SHORT, M. P., FLEET C., and BOHN, M. C. (1997). Human fetal astrocytes as an ex vivo gene therapy vehicle for delivering biologically active nerve growth factor. Hum. Gene Ther. 8, 331–339.

LUNDBERG, C., HORELLOU, P., MALLET, J., and BJÖIRKLUND, A. (1996). Generation of DOPA-producing astrocytes by retroviral transduction of the human tyrosine hydroxylase gene: in vitro characterization and in vivo effects in the rat Parkinson model. Exp. Neurol. 139, 39–53.

MARON, A., HAVAUX, N., LE ROUX, A., KNOOPS, B., PERRICAUDET, M., and OCTAVE, J. N. (1997). Differential toxicity of ganciclovir for rat neurons and astrocytes in primary culture following adenovirus-mediated transfer of the HSVtk gene. Gene Ther. 4, 25–3 1.

MARTINEZ-SERRANO, A., and BJORKLUND, A. (1997). Immortalized neural progenitor cells for CNS gene transfer and repair. Trends Neurosci. 20, 530–538.

McCARTHY, M., WOOD, C., FEDOSEYEVA, L., and WHITTEMORE. S. C. (1995). Media components influence viral gene expression assays in human fetal astrocyte cultures. J. Neurovirol. 1, 275–285.

MILLER, N., and WHELAN, J. (1997) Progress in transcriptionally targeted and regulatable vectors for genetic therapy. Hum. Gene Ther. 8, 803–815.

OLANOW, C. W., KORDOWE,R J. H., and FREEMAN, T. B. (1996). Fetal nigral transplantation as a therapy for Parkinson's disease. Trends Neurosci. 19, 102–109.

PERZELOVA, A. and MARES, V. (1993). Appearance of GFAP-positive cells in adult human brain cultures spontaneously decelerated in growth. Glia 7, 237–244.

PUNDT, L. L., KONDOH, T., and LOW, W. C. (1995). The fate of human glial cells following transplantation in normal rodents and rodent models of neurodegenerative disease. Brain Res. 695, 25–36.

REINHARD Jr, J. F., SMITH, G. K., and NICHOL, C. A. (1986). A rapid and sensitive assay for tyrosine-3-monooxygenase based upon the release of $^3H_2O$ and adsorption of [$^3H$]-tyrorine by charcoal. Life Sci. 39, 2185–2189.

RIDET, J. L., MALHOTRA, S. K., PRIVAT. A., and GAGE, F. H. (1997). Reactive astrocytes: cellular and molecular cues to biological function. Trends Neurosci. 20, 570–577.

RIDOUX, V., ROBERT, J. J., ZHANG. X., PERRICAUDET, M., MALLET, J., and LE GAL LA SALLE, G. (1994). The use of adenovirus vectors for intracerebral grafting of transfected nervous cells. NeuroReport 5, 801–804.

SABATE, O., HORELLOU, P., VIGNE, E., COLIN, P., PERRICAUDET, M., BUC-CARON, M. H., and MALLET, J. (1995). Transplantation to the rat brain of human neural progenitors that were genetically modified using adenovirus. Nature Genet. 9, 256–260.

SAEZ, E., NO, D., WEST, A., and EVANS, R. M. (1997) Inducible gene expression in mammalian cells and transgenic mice. Curr. Opin. Biotechnol. 8. 608–616.

SHOCKETT, P., DIFILIPPANTONIO, M., HELLMAN, N., and SCHATZ, D. G. (1995). A modified tetracycline-regulated system provides autoregulatory, inducible gene expression in cultured cells and transgenic mice. Proc. Natl. Acad. Sci. USA 92, 6522–6526.

STACHOWIAK, M. K., MOFFETT, J., MAHER, P., TUCHOLSKI J., and STACHOWIAK, E. K. (1997). Growth factor regulation f cell growth and proliferation in the nervous system. Mol. Neurobiol. 15, 257–283.

STREIT, W. J. (1990). An improved staining method for rat microglial cells using the lectin from *Griffonia simplicifolia* (GSA I-B4). J. Histochem. Cytochem. 38, 1683–1686.

TAYLOR, R. (1997). Cell vehicles for gene transfer to the brain. Neuromuscul. Dis. 7, 343–351.

WOLFF J. F., FISHER, L. J., XU, L., JINNAH, H. A., LANGLAIS, P. J., IUVONE, P. M., O'MALLEY, K. L., ROSENBERG, M. B., SHIMOHAMA, S., FRIEDMANN, T., and GAGE, F. H. (1989). Grafting fibroblasts genetically modified to produce L-Dopa in a rat model of Parkinson's disease. Proc. Natl. Acad. Sci. USA 86, 9011–9014.

YONG, V. W., MOUMDJIAN, R., YONG, F. P., RUIJS, T. C. G., FREEDMAN, M. S., CASHMAN, N., and ANTEL, J. P. (1991). Gamma-interferon promotes proliferation of adult human astrocytes in vitro and reactive gliosis in the adult mouse brain in vivo. Proc. Natl. Acad. Sci. USA 88, 7016–7020.

YONG, V. W., TEJADA-BERGES, T., GOODYER, C. G., ANTEL, J. P., and YONG, F. P. (1992). Differential proliferative response of human and mouse astrocytes to gamma-interferon. Glia 6, 269–280

YOSHIMOTO, Y., LIN, Q., COLLIER, T., FRIM, D., BREAKFIELD, X. O., and BOHN, M. C. (1995). Astrocytes retrovirally transduced with BDNF elicit behavioral improvement in a rat model of Parkinson's disease. Brain Res. 691, 25–36.

What is claimed is:

1. A method of producing an essentially pure population of astrocytes which are essentially free of microglial cells, the method comprising:

a) preparing a mixture of astrocytes and microglial cells by dissociation of tissue obtained by surgical resection from a patient, and directly introducing the prepared mixture of astrocytes and microglial cells to a culture vessel, b) incubating the prepared mixture of astrocytes and micioglial cells from step a) under conditions enabling attachment of the astrocytes to the culture vessel, and c) removing cells which have not attached to the culture vessel at a time of about 48 hours from the introduction of the prepared mixture of astrocytes and microglial cells to the culture vessel.

2. The method according to claim 1, wherein the astrocytes are human astrocytes.

3. The method according to claim 2, wherein the human astrocytes are human adult astrocytes.

4. The method according to claim 1, wherein unattached cells are removed from the culture vessel by a change of culture media.

5. The method according to claim 1, further comprising a step d) of introducing a nucleic acid into the astrocytes.

6. The method according to claim 5, wherein the nucleic acid is introduced into the astrocytes with a viral vector.

7. The method according to claim 6, wherein the viral vector is selected from the group consisting of adenovirus, Herpes virus, Adeno-Associated Virus, retrovirus and vaccinia virus.

8. The method according to claim 7, wherein the viral vector is a replication defective adenoviral vector.

9. The method according to claim 5, wherein the nucleic acid is introduced into the astrocytes by calcium-phosphate precipitation, liposome-mediated transfection, cationic lipid transfection, or lipopolyamine-mediated transfection.

10. The method according to claim 5, wherein the nucleic acid encodes a neuroactive substance.

* * * * *